(12) United States Patent
Klyamkin et al.

(10) Patent No.: US 9,651,523 B2
(45) Date of Patent: May 16, 2017

(54) SYSTEM FOR MEASURING THE CONCENTRATION OF MAGNETIC BALLAST IN A SLURRY

(71) Applicant: Evoqua Water Technologies LLC, Warrendale, PA (US)

(72) Inventors: Simone Klyamkin, Brighton, MA (US); Steven E. Woodard, Cumberland, ME (US); Frank Federico, Winchester, MA (US); Colin' M. McKean, Wauwatosa, WI (US)

(73) Assignee: Evoqua Water Technologies LLC, Warrendale, PA (US)

(*) Notice: Subject to any disclaimer, the term of this patent is extended or adjusted under 35 U.S.C. 154(b) by 109 days.

(21) Appl. No.: 14/428,740

(22) PCT Filed: Sep. 26, 2013

(86) PCT No.: PCT/US2013/062045
§ 371 (c)(1),
(2) Date: Mar. 17, 2015

(87) PCT Pub. No.: WO2014/052674
PCT Pub. Date: Apr. 3, 2014

(65) Prior Publication Data
US 2015/0233867 A1    Aug. 20, 2015

Related U.S. Application Data

(60) Provisional application No. 61/705,868, filed on Sep. 26, 2012.

(51) Int. Cl.
*G01N 27/74* (2006.01)
*G01N 33/18* (2006.01)

(52) U.S. Cl.
CPC ............. *G01N 27/74* (2013.01); *G01N 33/18* (2013.01)

(58) Field of Classification Search
CPC ................................ G01N 27/74; G01N 33/18
(Continued)

(56) References Cited

U.S. PATENT DOCUMENTS 438,579 A    10/1890   Faunce et al.
531,183 A    12/1894   Harris
(Continued)

FOREIGN PATENT DOCUMENTS

CN    1686862 A    10/2005
CN    101186410 A    5/2008
(Continued)

OTHER PUBLICATIONS www.ingentaconnect.com/content/wef/wefproc/2009/00002009/00000004/art0020, downloaded Dec. 16, 2012.
(Continued)

*Primary Examiner* — Christopher Mahoney

(57) ABSTRACT

A system and method for measuring the concentration of magnetic ballast in a slurry to be analyzed is provided. A detection conduit is provided and configured to receive a slurry to be analyzed. The detection conduit may be surrounded by a set of detection coaxial coils. A reference set of two coaxial coils is also provided. A power source is provided for establishing an electrical current. A measurement subsystem for measuring the differential induced voltage between detection and reference coils is provided to determine the concentration of the magnetic ballast in the slurry.

11 Claims, 7 Drawing Sheets

(58) Field of Classification Search
USPC ............... 324/204, 209, 220, 234, 236, 239; 73/61.41, 579, 53.07
See application file for complete search history.

(56) References Cited

U.S. PATENT DOCUMENTS

| | | |
|---|---|---|
| 653,010 A | 7/1900 | Koyl |
| 728,062 A | 5/1903 | Wilson |
| 1,064,807 A | 6/1913 | Yost |
| 1,310,461 A | 7/1919 | Williams |
| 1,383,287 A | 7/1921 | Campbell |
| 1,401,288 A | 12/1921 | Sodeau |
| 1,948,080 A | 2/1934 | Thomas |
| 2,065,123 A | 12/1936 | Downes |
| 2,129,267 A | 9/1938 | Fischer |
| 2,232,294 A | 2/1941 | Urbain et al. |
| 2,232,296 A | 2/1941 | Urbain et al. |
| 2,268,461 A | 12/1941 | Nichols |
| 2,326,575 A | 8/1943 | Stearns |
| 2,359,748 A | 10/1944 | Clemens |
| 2,391,494 A | 12/1945 | Walker |
| 2,401,924 A | 6/1946 | Goetz |
| 2,564,515 A | 8/1951 | Vogel |
| 2,597,561 A | 5/1952 | Blind |
| 2,652,925 A | 9/1953 | Vermeiren |
| 2,713,028 A | 7/1955 | Jenks |
| 2,758,715 A | 8/1956 | Fowler |
| 2,825,464 A | 3/1958 | Mack |
| 2,912,107 A | 11/1959 | Palm |
| 2,945,590 A | 7/1960 | Stearns |
| 3,066,095 A | 11/1962 | Hronas |
| 3,080,264 A | 3/1963 | Zimmie |
| 3,142,638 A | 7/1964 | Blaisdell et al. |
| 3,228,878 A | 1/1966 | Moody |
| 3,350,302 A | 10/1967 | Demeter et al. |
| 3,575,852 A | 4/1971 | Hughes |
| 3,617,561 A | 11/1971 | Fanselow |
| 3,622,461 A | 11/1971 | Wagner et al. |
| 3,627,678 A | 12/1971 | Marston et al. |
| 3,676,337 A | 7/1972 | Kolm |
| 3,690,454 A | 9/1972 | Bekhtle et al. |
| 3,693,795 A | 9/1972 | Robinson et al. |
| 3,697,420 A | 10/1972 | Blaisdell et al. |
| 3,703,958 A | 11/1972 | Kolm |
| 3,767,351 A | 10/1973 | Blaser |
| 3,819,589 A | 6/1974 | Fauke et al. |
| 3,856,666 A | 12/1974 | Yashima et al. |
| 3,886,064 A | 5/1975 | Kosonen |
| 3,887,457 A | 6/1975 | Marston et al. |
| 3,920,543 A | 11/1975 | Marston et al. |
| 3,929,632 A | 12/1975 | Buriks et al. |
| 3,929,635 A | 12/1975 | Buriks et al. |
| 3,950,319 A | 4/1976 | Schmidt et al. |
| 3,951,807 A | 4/1976 | Sanderson |
| 3,959,133 A | 5/1976 | Fulton |
| 3,983,033 A | 9/1976 | de Latour |
| 4,024,040 A | 5/1977 | Phalangas et al. |
| 4,025,432 A | 5/1977 | Nolan et al. |
| 4,033,864 A | 7/1977 | Nolan et al. |
| 4,046,681 A | 9/1977 | Marston et al. |
| 4,066,991 A | 1/1978 | Marston et al. |
| 4,089,779 A | 5/1978 | Neal |
| 4,110,208 A | 8/1978 | Neal |
| 4,139,456 A | 2/1979 | Yabuuchi et al. |
| 4,142,970 A | 3/1979 | von Hagel et al. |
| 4,151,090 A | 4/1979 | Brigante |
| 4,153,559 A | 5/1979 | Sanderson |
| 4,167,480 A | 9/1979 | Mach |
| 4,176,042 A | 11/1979 | Fahlstrom |
| 4,190,539 A | 2/1980 | Besik |
| 4,193,866 A | 3/1980 | Slusarczuk et al. |
| 4,204,948 A | 5/1980 | Wechsler et al. |
| 4,274,968 A | 6/1981 | Grutsch et al. |
| 4,290,898 A | 9/1981 | von Hagel et al. |
| 4,297,484 A | 10/1981 | Quinlan |
| 4,320,012 A | 3/1982 | Palm et al. |
| 4,339,347 A | 7/1982 | Quinlan |
| 4,341,657 A | 7/1982 | Quinlan |
| 4,343,730 A | 8/1982 | Becker et al. |
| 4,357,237 A | 11/1982 | Sanderson |
| 4,358,382 A | 11/1982 | Quinlan |
| 4,359,382 A | 11/1982 | Morgan |
| 4,377,483 A | 3/1983 | Yamashita et al. |
| 4,388,195 A | 6/1983 | von Hagel et al. |
| 4,402,833 A | 9/1983 | Bennett et al. |
| 4,440,649 A | 4/1984 | Loftin et al. |
| 4,454,047 A | 6/1984 | Becker et al. |
| 4,465,597 A | 8/1984 | Herman et al. |
| 4,482,459 A | 11/1984 | Shiver |
| 4,502,958 A | 3/1985 | Sasaki |
| 4,522,643 A | 6/1985 | Quinlan |
| 4,563,286 A | 1/1986 | Johnson et al. |
| 4,579,655 A | 4/1986 | Louboutin et al. |
| 4,588,508 A | 5/1986 | Allenson et al. |
| 4,595,506 A | 6/1986 | Kneer |
| 4,626,354 A | 12/1986 | Hoffman et al. |
| 4,654,139 A | 3/1987 | Baba et al. |
| 4,655,933 A | 4/1987 | Johnson et al. |
| 4,686,035 A | 8/1987 | Estabrook |
| 4,689,154 A | 8/1987 | Zimberg |
| 4,699,951 A | 10/1987 | Allenson et al. |
| 4,735,725 A | 4/1988 | Reischl et al. |
| 4,752,401 A | 6/1988 | Bodenstein |
| 4,765,900 A | 8/1988 | Schwoyer et al. |
| 4,765,908 A | 8/1988 | Monick et al. |
| 4,783,265 A | 11/1988 | Timmons |
| 4,795,557 A | 1/1989 | Bourbigot et al. |
| 4,827,890 A | 5/1989 | Pociask et al. |
| 4,843,105 A | 6/1989 | Reischl et al. |
| 4,849,128 A | 7/1989 | Timmons et al. |
| 4,851,123 A | 7/1989 | Mishra |
| 4,864,075 A | 9/1989 | Thompson et al. |
| 4,872,993 A | 10/1989 | Harrison |
| 4,874,508 A | 10/1989 | Fritz |
| 4,882,064 A | 11/1989 | Dixon et al. |
| 4,921,597 A | 5/1990 | Lurie |
| 4,921,613 A | 5/1990 | Nordberg et al. |
| 4,927,543 A | 5/1990 | Bablon et al. |
| 4,938,876 A | 7/1990 | Ohsol |
| 4,940,550 A | 7/1990 | Watson |
| 4,944,278 A | 7/1990 | Woodard |
| 4,944,279 A | 7/1990 | Woodard |
| 4,956,099 A | 9/1990 | Thompson et al. |
| 4,981,593 A | 1/1991 | Priestley et al. |
| 5,009,791 A | 4/1991 | Lin et al. |
| 5,013,451 A | 5/1991 | Thompson et al. |
| 5,019,274 A | 5/1991 | Thompson et al. |
| 5,023,012 A | 6/1991 | Buchan et al. |
| 5,026,483 A | 6/1991 | Thompson et al. |
| 5,055,194 A | 10/1991 | Goetz et al. |
| 5,064,531 A | 11/1991 | Wang et al. |
| 5,069,783 A | 12/1991 | Wang et al. |
| 5,084,733 A | 1/1992 | Katoh et al. |
| 5,089,120 A | 2/1992 | Eberhardt |
| 5,089,227 A | 2/1992 | Thompson et al. |
| 5,089,619 A | 2/1992 | Thompson et al. |
| 5,112,494 A | 5/1992 | Yan |
| 5,112,499 A | 5/1992 | Murray et al. |
| 5,126,050 A | 6/1992 | Irvine et al. |
| 5,149,438 A | 9/1992 | Hebert |
| 5,187,326 A | 2/1993 | Shirai |
| 5,234,603 A | 8/1993 | Potts |
| 5,266,200 A | 11/1993 | Reid |
| 5,298,168 A | 3/1994 | Guess |
| 5,307,938 A | 5/1994 | Lillmars |
| 5,310,642 A | 5/1994 | Vargas et al. |
| 5,369,072 A | 11/1994 | Benjamin et al. |
| 5,377,845 A | 1/1995 | Hamen et al. |
| 5,383,539 A | 1/1995 | Bair et al. |
| 5,395,527 A | 3/1995 | Desjardins |
| 5,397,476 A | 3/1995 | Bradbury et al. |
| 5,462,670 A | 10/1995 | Guess |
| 5,545,330 A | 8/1996 | Ehrlich |
| 5,560,493 A | 10/1996 | Perry |

(56) References Cited

U.S. PATENT DOCUMENTS

| | | |
|---|---|---|
| 5,593,590 A | 1/1997 | Steyskal |
| 5,595,666 A | 1/1997 | Kochen et al. |
| 5,596,392 A | 1/1997 | Danzuka |
| 5,597,479 A | 1/1997 | Johnson |
| 5,616,241 A | 4/1997 | Khudenko |
| 5,616,250 A | 4/1997 | Johnson et al. |
| 5,637,221 A | 6/1997 | Coyne |
| 5,693,461 A | 12/1997 | Bagchi et al. |
| 5,702,809 A | 12/1997 | Tixier et al. |
| 5,730,864 A | 3/1998 | Delsalle et al. |
| 5,731,134 A | 3/1998 | Honan et al. |
| 5,766,459 A | 6/1998 | Adams, Jr. |
| 5,770,091 A | 6/1998 | Binot et al. |
| 5,779,908 A | 7/1998 | Anderson et al. |
| 5,800,717 A | 9/1998 | Ramsay et al. |
| 5,805,965 A | 9/1998 | Tsuda et al. |
| 5,840,195 A | 11/1998 | Delsalle et al. |
| 5,856,072 A | 1/1999 | Leone et al. |
| 5,893,355 A | 4/1999 | Glover et al. |
| 5,925,290 A | 7/1999 | Hills |
| 5,976,375 A | 11/1999 | Dorica et al. |
| 5,976,771 A | 11/1999 | Kosugi et al. |
| 6,010,631 A | 1/2000 | Delsalle et al. |
| 6,030,761 A | 2/2000 | Taguchi et al. |
| 6,093,318 A | 7/2000 | Saho et al. |
| 6,099,738 A | 8/2000 | Wechsler et al. |
| 6,149,014 A | 11/2000 | Mankosa et al. |
| 6,151,467 A | 11/2000 | Yamaguchi |
| 6,160,976 A | 12/2000 | Karakama et al. |
| 6,185,393 B1 | 2/2001 | Karakama et al. |
| 6,210,587 B1 | 4/2001 | Vion |
| 6,210,588 B1 | 4/2001 | Vion |
| 6,217,773 B1 | 4/2001 | Graham |
| 6,221,253 B1 | 4/2001 | Fukase et al. |
| 6,221,262 B1 | 4/2001 | MacDonald et al. |
| 6,228,269 B1 | 5/2001 | Cort |
| 6,228,565 B1 | 5/2001 | Ohzeki et al. |
| 6,251,576 B1 | 6/2001 | Taguchi et al. |
| 6,277,285 B1 | 8/2001 | Vion |
| 6,290,849 B1 | 9/2001 | Rykaer et al. |
| 6,379,549 B1 | 4/2002 | LePoder et al. |
| 6,383,370 B1 | 5/2002 | Keever et al. |
| 6,386,781 B1 | 5/2002 | Gueret |
| 6,406,624 B1 | 6/2002 | DeVos |
| 6,423,485 B1 | 7/2002 | Yamada et al. |
| 6,432,303 B1 | 8/2002 | Chesner et al. |
| 6,447,686 B1 | 9/2002 | Choi et al. |
| 6,472,132 B1 | 10/2002 | Yamada et al. |
| 6,478,955 B1 | 11/2002 | Saho et al. |
| 6,485,652 B1 | 11/2002 | Le Poder et al. |
| 6,517,714 B2 | 2/2003 | Streat |
| 6,576,145 B2 | 6/2003 | Conaway et al. |
| 6,613,232 B2 | 9/2003 | Chesner et al. |
| 6,645,386 B1 | 11/2003 | Moreau et al. |
| 6,689,277 B2 | 2/2004 | Streat |
| 6,692,173 B2 | 2/2004 | Gueret |
| 6,706,467 B2 | 3/2004 | Howe et al. |
| 6,740,245 B2 | 5/2004 | Johnson |
| 6,759,018 B1 | 7/2004 | Arno et al. |
| 6,783,679 B1 | 8/2004 | Rozich |
| 6,811,885 B1 | 11/2004 | Andriessen et al. |
| 6,824,692 B2 | 11/2004 | Binot et al. |
| 6,832,691 B2 | 12/2004 | Miles et al. |
| 6,875,351 B2 | 4/2005 | Arnaud |
| 6,878,856 B2 | 4/2005 | Kim et al. |
| 6,896,815 B2 | 5/2005 | Cort |
| 6,902,678 B2 | 6/2005 | Tipton |
| 6,919,031 B2 | 7/2005 | Blumenschein et al. |
| 6,923,901 B2 | 8/2005 | Leffler et al. |
| 6,960,294 B2 | 11/2005 | Arnaud |
| 6,966,993 B2 | 11/2005 | Binot |
| 6,968,138 B2 | 11/2005 | Akutsu |
| 7,001,525 B2 | 2/2006 | Binot et al. |
| 7,083,715 B2 | 8/2006 | Binot |
| 7,153,431 B2 | 12/2006 | Daugherty |
| 7,160,448 B2 | 1/2007 | Johnson |
| 7,210,581 B2 | 5/2007 | Robinson et al. |
| 7,244,362 B2 | 7/2007 | Binot |
| 7,255,793 B2 | 8/2007 | Cort |
| 7,276,165 B2 | 10/2007 | Morgoun |
| 7,309,435 B2 | 12/2007 | Rozich |
| 7,311,841 B2 | 12/2007 | Binot et al. |
| 7,323,108 B1 | 1/2008 | Garbett et al. |
| 7,407,582 B2 | 8/2008 | Sun |
| 7,407,593 B2 | 8/2008 | Frederick, Jr. et al. |
| 7,438,817 B2 | 10/2008 | Nagghappan et al. |
| 7,449,105 B2 | 11/2008 | Hastings |
| 7,476,324 B2 | 1/2009 | Ciampi et al. |
| 7,494,592 B2 | 2/2009 | Deskins |
| 7,557,566 B2 * | 7/2009 | Kordonski ............ G01N 27/76 324/204 |
| 7,563,366 B2 | 7/2009 | Sun |
| 7,601,261 B2 | 10/2009 | Palacios Donaque |
| 7,608,190 B1 | 10/2009 | Banerjee et al. |
| 7,625,490 B2 | 12/2009 | Cort |
| 7,648,637 B1 | 1/2010 | Sauvignet et al. |
| 7,648,638 B2 | 1/2010 | Essemiani et al. |
| 7,651,620 B2 | 1/2010 | Vion |
| 7,678,278 B2 | 3/2010 | Binot et al. |
| 7,686,079 B2 | 3/2010 | Gamache et al. |
| 7,686,960 B2 | 3/2010 | Cort |
| 7,691,261 B2 | 4/2010 | Deskins |
| 7,691,269 B2 | 4/2010 | Cort |
| 7,695,623 B2 | 4/2010 | Woodard et al. |
| 7,695,630 B2 | 4/2010 | de Guevara |
| 7,704,390 B2 | 4/2010 | Leffler et al. |
| 7,704,399 B2 | 4/2010 | Condit |
| 7,722,843 B1 | 5/2010 | Srinivasachar |
| 7,729,778 B2 | 6/2010 | Eggers et al. |
| 7,820,025 B2 | 10/2010 | Ciampi et al. |
| 7,820,053 B2 | 10/2010 | Cort |
| 7,820,054 B2 | 10/2010 | Hastings et al. |
| 7,828,976 B2 | 11/2010 | Banerjee et al. |
| 8,012,582 B2 | 9/2011 | Luo et al. |
| 3,056,728 A1 | 11/2011 | Riise et al. |
| 8,198,887 B2 * | 6/2012 | Targosz ................ G01N 33/42 324/204 |
| 8,470,172 B2 | 6/2013 | Woodard et al. |
| 8,506,800 B2 | 8/2013 | Woodard et al. |
| 8,540,877 B2 | 9/2013 | Woodard |
| 2001/0030160 A1 | 10/2001 | Wechsler et al. |
| 2002/0003115 A1 | 1/2002 | Conaway et al. |
| 2002/0017483 A1 | 2/2002 | Chesner et al. |
| 2002/0030019 A1 | 3/2002 | Keever et al. |
| 2002/0054783 A1 | 5/2002 | Gueret |
| 2002/0088758 A1 | 7/2002 | Blumenschein et al. |
| 2002/0148780 A1 | 10/2002 | Tiemeyer |
| 2002/0158025 A1 | 10/2002 | Streat |
| 2002/0170816 A1 | 11/2002 | Leffler et al. |
| 2002/0185452 A1 | 12/2002 | Johnson |
| 2002/0190004 A1 | 12/2002 | Wechsler et al. |
| 2003/0082084 A1 | 5/2003 | Cort |
| 2003/0089667 A1 | 5/2003 | Binot et al. |
| 2003/0132160 A1 | 7/2003 | Khudenko |
| 2003/0150817 A1 | 8/2003 | Keever et al. |
| 2003/0222027 A1 | 12/2003 | Streat |
| 2003/0224301 A1 | 12/2003 | Howe et al. |
| 2004/0055959 A1 | 3/2004 | Wechsler et al. |
| 2004/0055961 A1 | 3/2004 | Binot |
| 2004/0060876 A1 | 4/2004 | Tipton |
| 2004/0129642 A1 | 7/2004 | Binot |
| 2004/0144730 A1 | 7/2004 | Binot et al. |
| 2004/0149653 A1 | 8/2004 | Johnson et al. |
| 2004/0206680 A1 | 10/2004 | Johnson |
| 2004/0206699 A1 | 10/2004 | Ho et al. |
| 2004/0213721 A1 | 10/2004 | Arno et al. |
| 2005/0005471 A1 | 1/2005 | Pan |
| 2005/0035030 A1 | 2/2005 | Oder et al. |
| 2005/0045534 A1 | 3/2005 | Kin et al. |
| 2005/0051488 A1 | 3/2005 | Nagghappan et al. |
| 2005/0101719 A1 | 5/2005 | Ishihara |
| 2005/0103719 A1 | 5/2005 | Binot et al. |
| 2005/0131266 A1 | 6/2005 | Carman et al. |
| 2005/0173354 A1 | 8/2005 | Binot et al. |

(56) References Cited

U.S. PATENT DOCUMENTS

| | | |
|---|---|---|
| 2005/0194311 A1 | 9/2005 | Rozich |
| 2005/0218056 A1 | 10/2005 | Binot |
| 2005/0230299 A1 | 10/2005 | Saho et al. |
| 2005/0258103 A1 | 11/2005 | Cort |
| 2005/0271575 A1 | 12/2005 | Ciampi et al. |
| 2005/0277712 A1 | 12/2005 | Daly |
| 2005/0282144 A1 | 12/2005 | Wechsler et al. |
| 2006/0006114 A1 | 1/2006 | Deskins |
| 2006/0018273 A1 | 1/2006 | Yamada et al. |
| 2006/0108273 A1 | 5/2006 | Perri et al. |
| 2006/0108283 A1 | 5/2006 | Johnson et al. |
| 2006/0138047 A1 | 6/2006 | Morgoun |
| 2006/0175252 A1 | 8/2006 | Upendrakumar et al. |
| 2006/0186056 A1 | 8/2006 | Ivan |
| 2006/0213832 A1 | 9/2006 | Hudson et al. |
| 2006/0254770 A1 | 11/2006 | Hou |
| 2006/0270888 A1 | 11/2006 | Carman et al. |
| 2006/0289357 A1 | 12/2006 | Wechsler et al. |
| 2007/0039894 A1 | 2/2007 | Cort |
| 2007/0062883 A1 | 3/2007 | Frederick et al. |
| 2007/0108132 A1 | 5/2007 | de Guevara |
| 2007/0114184 A1 | 5/2007 | Essemiani et al. |
| 2007/0119776 A1 | 5/2007 | Isaka et al. |
| 2007/0138093 A1 | 6/2007 | Bossler et al. |
| 2007/0163955 A1 | 7/2007 | Sun |
| 2008/0019780 A1 | 1/2008 | Hastings |
| 2008/0073267 A1 | 3/2008 | Cort |
| 2008/0073268 A1 | 3/2008 | Cort |
| 2008/0073270 A1 | 3/2008 | Smith |
| 2008/0073271 A1 | 3/2008 | Cort |
| 2008/0073278 A1* | 3/2008 | Cort .................. C02F 1/488 210/695 |
| 2008/0073279 A1 | 3/2008 | Cort |
| 2008/0073280 A1 | 3/2008 | Cort |
| 2008/0073281 A1 | 3/2008 | Cort |
| 2008/0073282 A1 | 3/2008 | Cort |
| 2008/0073283 A1 | 3/2008 | Cort |
| 2008/0073284 A1 | 3/2008 | Cort |
| 2008/0078721 A1 | 4/2008 | Binot et al. |
| 2008/0135491 A1 | 6/2008 | Cort |
| 2008/0150518 A1 | 6/2008 | Becker et al. |
| 2008/0156709 A1 | 7/2008 | Johnson |
| 2008/0164183 A1 | 7/2008 | Marston et al. |
| 2008/0164184 A1 | 7/2008 | Marston et al. |
| 2008/0203015 A1 | 8/2008 | Marston et al. |
| 2008/0210613 A1 | 9/2008 | Wechsler et al. |
| 2008/0217244 A1 | 9/2008 | Gaid |
| 2008/0257810 A1 | 10/2008 | Sun |
| 2008/0272065 A1 | 11/2008 | Johnson |
| 2008/0290030 A1 | 11/2008 | Nagghappan et al. |
| 2008/0296228 A1 | 12/2008 | Sauvignet et al. |
| 2008/0314820 A1 | 12/2008 | Prulhiere et al. |
| 2008/0314830 A1 | 12/2008 | Banerjee et al. |
| 2009/0047076 A1 | 2/2009 | Hastings |
| 2009/0050570 A1 | 2/2009 | Sauvignet |
| 2009/0065404 A1 | 3/2009 | Paspek, Jr. et al. |
| 2009/0084730 A1 | 4/2009 | Mabille et al. |
| 2009/0098262 A1 | 4/2009 | Mabille et al. |
| 2009/0127180 A1 | 5/2009 | Deskins |
| 2009/0178979 A1 | 7/2009 | Hastings et al. |
| 2009/0189599 A1 | 7/2009 | Fujii et al. |
| 2009/0206040 A1 | 8/2009 | Berg et al. |
| 2009/0218281 A1 | 9/2009 | Sauvignet et al. |
| 2009/0261037 A1 | 10/2009 | Clifford, III et al. |
| 2009/0272693 A1 | 11/2009 | Mabille et al. |
| 2009/0299143 A1 | 12/2009 | Conlon et al. |
| 2009/0301948 A1 | 12/2009 | Essemiani et al. |
| 2009/0308815 A1 | 12/2009 | Sauvignet et al. |
| 2010/0038081 A1 | 2/2010 | Gamache et al. |
| 2010/0047671 A1 | 2/2010 | Chiang et al. |
| 2010/0057085 A1 | 3/2010 | Holcomb et al. |
| 2010/0072142 A1 | 3/2010 | Lean et al. |
| 2010/0096335 A1 | 4/2010 | Sauvignet et al. |
| 2010/0101309 A1 | 4/2010 | Klyamkin et al. |
| 2010/0102006 A1 | 4/2010 | Quevillon |
| 2010/0155327 A1 | 6/2010 | Woodard et al. |
| 2010/0213123 A1 | 8/2010 | Marston et al. |
| 2010/0219372 A1 | 9/2010 | Hook et al. |
| 2010/0251571 A1 | 10/2010 | Woodard |
| 2010/0274209 A1 | 10/2010 | Roe et al. |
| 2011/0036771 A1 | 2/2011 | Woodard |
| 2011/0147304 A1 | 6/2011 | Sauvignet et al. |
| 2012/0067824 A1 | 3/2012 | Berg et al. |
| 2013/0020255 A1 | 1/2013 | Woodard |
| 2016/0221853 A1* | 8/2016 | Cort .................. C02F 11/12 |

FOREIGN PATENT DOCUMENTS

| | | |
|---|---|---|
| CN | 101244884 A | 8/2008 |
| CN | 101296870 A | 10/2008 |
| CN | 101309870 A | 11/2008 |
| DE | 19600647 A1 | 7/1997 |
| EP | 0087223 A1 | 8/1983 |
| EP | 0139572 A1 | 5/1985 |
| EP | 266098 A2 | 5/1988 |
| EP | 392321 A1 | 10/1990 |
| EP | 392322 A1 | 10/1990 |
| EP | 1785400 A1 | 5/2007 |
| EP | 2165980 A1 | 3/2010 |
| FR | 1411792 A | 9/1965 |
| FR | 2378550 A1 | 8/1978 |
| FR | 2719235 A1 | 11/1995 |
| JP | 07-299495 A | 11/1995 |
| JP | 08-257583 A | 10/1996 |
| JP | 11-169866 A | 6/1999 |
| JP | 2000-233198 A | 8/2000 |
| JP | 2001-170404 A | 6/2001 |
| JP | 2003-010874 A | 1/2003 |
| SU | 1136839 A1 | 1/1985 |
| WO | 9312041 A1 | 6/1993 |
| WO | 9735654 A1 | 10/1997 |
| WO | 9735655 A1 | 10/1997 |
| WO | 9803433 A1 | 1/1998 |
| WO | 9919261 A1 | 4/1999 |
| WO | 9931016 A1 | 6/1999 |
| WO | 0114260 A1 | 3/2001 |
| WO | 0128931 A1 | 4/2001 |
| WO | 0140121 A1 | 6/2001 |
| WO | 0200556 A1 | 1/2002 |
| WO | 0242223 A1 | 5/2002 |
| WO | 2005077835 A1 | 8/2005 |
| WO | 2005087381 A1 | 9/2005 |
| WO | 2006008634 A2 | 8/2006 |
| WO | 2006102362 A2 | 9/2006 |
| WO | 2007059141 A2 | 5/2007 |
| WO | 2007098298 A2 | 8/2007 |
| WO | 2007103409 A2 | 9/2007 |
| WO | 2008022192 A2 | 2/2008 |
| WO | 2008039711 A2 | 4/2008 |
| WO | 2008039936 A2 | 4/2008 |
| WO | 2008085196 A2 | 7/2008 |
| WO | 2008085197 A1 | 7/2008 |
| WO | 2008086009 A1 | 7/2008 |
| WO | 2008086010 A1 | 7/2008 |
| WO | 2009083346 A1 | 7/2009 |
| WO | 2010027895 A2 | 3/2010 |
| WO | 2010081903 A1 | 7/2010 |
| WO | 2010086249 A1 | 8/2010 |
| WO | 2011005927 A1 | 1/2011 |
| WO | 2011031305 A1 | 3/2011 |

OTHER PUBLICATIONS

Renjun, Xiong, Chinese Doctoral Dissertations & Master's Theses Full-text Database (Master) Engineering Science and Technology I, pp. B027-173, Sep. 15, 2004 (English Abstract, 2 pages).

Buchanan et al., "Aerobic Treatment of Wastewater and Aerobic Treatment Units," University Curriculum Development for Decentralized Wastewater Management Aerobic Treatment of Wastewater and Aerobic Treatment Units Buchanan and Seabloom, p. i-v and 1-22, Nov. 2004, [Retrieved on Mar. 9, 2011].

(56) References Cited

OTHER PUBLICATIONS

Catlow et al. "Ballasted Biological Treatment Process Removes Nutrients and Doubles Plant Capacity". WEFTEC Conference (Oct. 2008).
http://www.envirosim.com/includes/weftec08.htm, downloaded Dec. 16, 2012.
Kolm et al., "High Gradient Magnetic Separation," Scientific American, Nov. 1975, vol. 233, No. 5, 10 pages (unnumbered).
Lubenow et al. "Maximizing Nutrient Removal in an Existing SBR with a Full-Scale BioMag Demonstration". WEFTEC Conference. Date Unknown.
Moody et al. "Beyond Desktop Evaluation: Key Design Criteria for Mixing and Settling of Magnetite-Impregnated Mixed Liquor". WEFTEC Conference 2011.
Raskin et al., "Quantification of Methanogenic Groups in Anaerobic Biological Reactors by Oligonucleotide Probe Hybridization," Applied and Environmental Microbiology, Apr. 1994, vol. 60, No. 4, pp. 1241-1248.
Sakai et al., "A Sewage Treatment Process Using Highly Condensed Activated Sludge with an Apparatus for Magnetic Separation," 1994, Journal of Fermentation and Bioengineering, vol. 78, No. 1, pp. 120-122.
Sakai et al., "Magnetic Forced Sedimentation of Flocs in Activated Sludge Supplemented with Ferromagnetic Powder of Iron Oxide," 1991, Journal of Fermentation and Bioengineering, vol. 71, No. 3, pp. 208-210.
Sakai et al., "Recovery and Reuse of Ferromagnetic Powder Supplemented in Activated Sludge for Magnetic Separation," Dept. of Applied Chemistry, Faculty of Engineering, Utsunomiya University, Japan, Submitted: Jun. 28, 1991; Accepted: Oct. 22, 1991, pp. 1-11. Japanese language original (pp. 52-56), and translated English language copy (pp. 1-11).
Sakai et al., "Sewage Treatment under Conditions of Balancing Microbial Growth and Cell Decay with a High concentration of Activated Sludge Supplemented with Ferromagnetic Powder," 1992, Journal of Fermentation and Bioengineering, vol. 74, No. 6, pp. 413-315.
Sakai et al., "Simultaneous Removal of Organic and Nitrogen Compounds in Intermittently Aerated Activated Sludge Process Using Magnetic Separation," 1997, Technical Note Wat. Res., vol. 31, No. 8, pp. 2113-2116.
Tozer, "Study of Five Phosphorus Removal Processes," The Georgia Operator, vol. 45, No. (Winter 2008).

* cited by examiner

SYSTEM FOR MEASURING THE CONCENTRATION OF MAGNETIC BALLAST IN A SLURRY

FIELD OF THE INVENTION

This invention relates to a system and method for measuring the concentration of magnetic ballast in a slurry, for example a static or non-moving slurry.

SUMMARY OF THE DISCLOSURE

A system for measuring a concentration of magnetic ballast in a slurry is provided. The system comprises a detection conduit surrounded by a first detection coil, the detection conduit configured to receive the slurry, and the first detection coil comprising a first section and a second section both positioned coaxially along the detection conduit. The system further comprises a reference conduit surrounded by a first reference coil, and a second detection coil surrounding the detection conduit and positioned between the first and second sections of the first detection coil along a common axis of the detection conduit. The system further comprises a second reference coil surrounding the reference conduit and positioned in proximity to the first reference coil, and an AC power source configured to generate a magnetic field in the first detection coil and the first reference coil. The system further comprises a measurement device configured to measure a differential induced voltage between the second detection coil and the second reference coil to determine the concentration of the magnetic ballast in the slurry based on the measured differential induced voltage.

The slurry may be a static slurry or a moving slurry. The first detection coil and the first reference coil may be symmetrical. The first and second detection coils and the first and second reference coils may be positioned on a common plane of symmetry perpendicular to each other. The first and second detection coils and the first reference coil may be located on a common plane of symmetry parallel to each other. The first and second detection coils are identical to the first and second reference coils. The system may be configured to measure a concentration of magnetic ballast in a range of about 0.1 mg/l to about 500,000 mg/l. The differential induced voltage between the second detection coil and the second reference coil voltage may be proportional to the concentration of the magnetic ballast in the slurry. The measured voltage of the second detection coil may be proportional to the concentration of the magnetic ballast in the slurry.

A method for measuring a concentration of magnetic ballast in a slurry may be provided. The method comprises providing a system comprising a detection conduit surrounded by a first detection coil, comprising a first section and a second section both positioned coaxially along the detection conduit; a reference conduit surrounded by a first reference coil; a second detection coil surrounding the detection conduit and positioned between the first and second sections of the first detection coil along a common axis of the detection conduit; and a second reference coil surrounding the reference conduit and positioned in proximity to the first reference coil. The method comprises introducing the slurry into the detection conduit and generating a magnetic field in the first detection coil and the first reference coil. The method further comprises measuring an induced differential voltage between the second detection coils and the second reference coil to determine the concentration of the magnetic ballast in the slurry based on the measured differential induced voltage.

Introducing the slurry into the detection conduit may comprise at least partially immersing the system in a component of a wastewater treatment system. The component may include a component selected from the group consisting of a reaction tank, a mixing tank, and aeration tank, a settling tank, a clarifier, a conduit, line or pipe, an impregnation subsystem, a return activated sludge subsystem, a weighting agent recovery subsystem, a wasting system, and combinations thereof. The concentration of the magnetic ballast in the slurry is in a range of about 0.1 mg/l to about 500,000 mg/l.

DESCRIPTION OF THE DRAWINGS

The accompanying drawings are not intended to be drawn to scale. For purposes of clarity, not every component may be labeled in the drawings, nor is every component of each embodiment of the disclosure shown where illustration is not necessary to allow those of ordinary skill in the art to understand the disclosure.

In the drawings.

DETAILED DESCRIPTION

Figure 1:
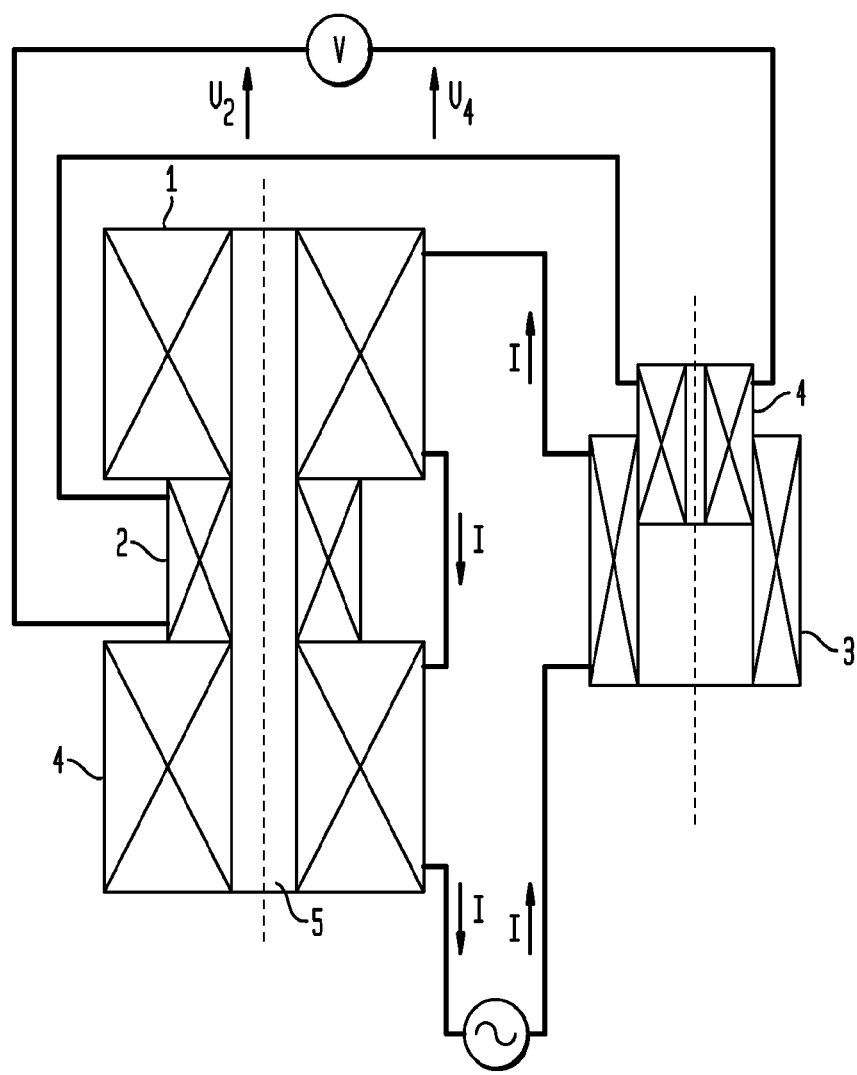
FIG. 1 presents a schematic of an example of a system for measuring the concentration of magnetic ballast.

Some wastewater treatment systems use magnetically separable particles as a settling aid. These particles may include magnetic ballast. The magnetic ballast may be magnetite, which may become enmeshed into a chemical and/or biological floc in a wastewater treatment process. The operation of ballasted wastewater treatment systems requires monitoring, automatically or manually, the level of the magnetic ballast in the slurry in the various components of the system. For example, the level or concentration of magnetic ballast may be monitored in the aeration tank or reaction tank or in a conduit between unit operations, such as between an aeration tank and a clarifier. The level or concentration of magnetic ballast may be monitored in a weighting agent (such as magnetite) impregnation subsystem, various areas of a clarifier, including the surface, sludge blanket and recycle slurry, various areas of magnetite recovery apparatus (magnetic drums, centrifugal separators, and other apparatus), various lines, pipes, conduits or holding tanks within the system, and the like. The range of magnetic ballast concentration that may require measurement may be a range of about 0.1 mg/l to about 500,000 mg/l.

In certain embodiments, systems and methods for measuring the concentration of magnetic ballast in various slurries of a ballasted wastewater system is provided. This may provide for more effective and efficient measurement of the concentration of magnetic ballast in the wastewater system, and may provide for accurate measurement of the concentration of a slurry, including static slurries and moving slurries.

Conventional systems and methods for determining the concentration of magnetic ballast in a slurry of a ballasted wastewater treatment system may include the extraction from the slurry, drying, and weighing of the pure magnetic ballast. The disadvantages of these conventional systems and methods are that they are time consuming and cumbersome. Some portion of fine magnetic ballast particles may be inevitably lost through the sludge, and may not be measured. Others systems and methods are based on the inductive method.

There are several issues that may arise from conventional systems that may use an inductive method. These may include unrestricted, non-uniform magnetic field applied to the slurry, unrestricted, non-uniform magnetic ballast distribution within a slurry sample, unrestricted mutual inductance between detection and reference coils, non-compensated, ambient, parasitic noise signal, unrestricted magnetic field applied to the magnetic slurry, which may result in nonlinear dependence of magnetic ballast properties vs. magnetic field intensity, and unrestricted AC power source voltage fluctuations.

The disadvantages of these systems and methods may provide inaccurate measurements, and indirect proportionality of measured induced voltage versus magnetic ballast concentration.

A system and method may be provided to offer a simplified measurement procedure, with higher accuracy, and direct proportionality of the measured signal versus magnetic ballast concentration in a range of about 0.1 mg/l to about 500,000 mg/l for a slurry, including static and moving slurries.

A system for measuring a concentration of magnetic ballast in a slurry is provided. The system may comprise a detection conduit surrounded by a first detection coil, the detection conduit configured to receive the slurry, and the first detection coil comprising a first section and a second section both positioned coaxially along the detection conduit. The system may further comprise a reference conduit surrounded by a first reference coil, and a second detection coil surrounding the detection conduit and positioned between the first and second sections of the first detection coil along a common axis of the detection conduit. The system may further comprise a second reference coil surrounding the reference conduit and positioned in proximity to the first reference coil, and an AC power source configured to generate a magnetic field in the first detection coil and the first reference coil. The system may further comprise a measurement device configured to measure a differential induced voltage between the second detection coil and the second reference coil to determine the concentration of the magnetic ballast in the slurry based on the measured differential induced voltage.

The system may include a permanent magnet surrounding one of the detection coils and the detection conduit for establishing a magnetic field. This may stop and collects magnetic ballast in the detection conduit so that the measurement device or subsystem may measure very low concentrations of magnetic ballast in the slurry.

A pumping subsystem may direct the moving slurry from a component of a wastewater treatment system to the detection conduit and, in some embodiments, back to the component of the wastewater treatment system.

The slurry of magnetic ballast may be a static slurry or a moving slurry. The system may automatically, continuously, and easily measure the concentration of magnetic ballast in the slurry.

In one embodiment, referring to FIG. 1, first detection coil 1 is a pair of two identical sections that are placed symmetrically; one on each side of the second detection coil 2 along a common axis of symmetry coaxially on a detection conduit 5, for example, a right cylinder. They are connected in series electrically and carry an equal electrical current (I) in the same direction. Such a design of the first detection coil provides the production of near uniform magnetic field in a region of the slurry that is positioned in the detection conduit 5, and that is detected by second detection coil 2. When a current is applied to first detection coil 1, a voltage is induced in detection coil 2. This voltage V2 will change in response to the presence of a magnetic ballast located in detection conduit 5 (of the right cylinder). If a magnetic ballast slurry is present in detection conduit 5 (right cylinder), the voltage V2 will change proportionally. First reference coil 3 and second reference coil 4 are also provided to generate a reference voltage V4. The current (I) is connected to the first reference coil 3 which will induce a voltage V4 in second reference coil 4. The two induced voltages V2 and V4 are compared to each other with a voltage measuring device or subsystem. The difference is used to determine the concentration of magnetic ballast present in the slurry. The measured voltage of the second detection coil may be proportional to the concentration of the magnetic ballast in the slurry.

The slurry has a tendency to settle by gravity and to distribute unevenly across and along the cylindrical sample volume. The higher the irregularity of magnetic field and/or magnetic ballast concentration, the more irregular the induced voltage is and therefore the measured value of the magnetic ballast concentration. The uniformity of the magnetic field is directly related to minimizing the measurement error.

In another embodiment, when measuring the concentration of magnetic ballast in a static slurry, the sample to be analyzed and first and second detection set of coils 1 and 2 are positioned horizontally to maximize magnetic ballast distribution uniformity along the sample volume. The even distribution of static slurry and magnetic ballast along and across the sample volume does not change during the time of measurement, provided the sample is well mixed prior to measurement.

In another embodiment, when measuring the concentration of magnetic ballast in a moving slurry, the analyzed sample and set of detection coils are positioned vertically to maximize magnetic ballast distribution uniformity across the sample volume. The even distribution of moving slurry and magnetic ballast along the sampling volume is provided by continual flow of the slurry.

In another embodiment, the AC power source is conditioned, for example, has the stabilized amplitude, for example about 10 to about 40 volts, or about 24 volts, a frequency in a range of about 0.1 to about 10,000 Hz, preferably about 400 Hz, and a sinusoidal shaped output current. This may minimize the measurement error.

Figure 2:
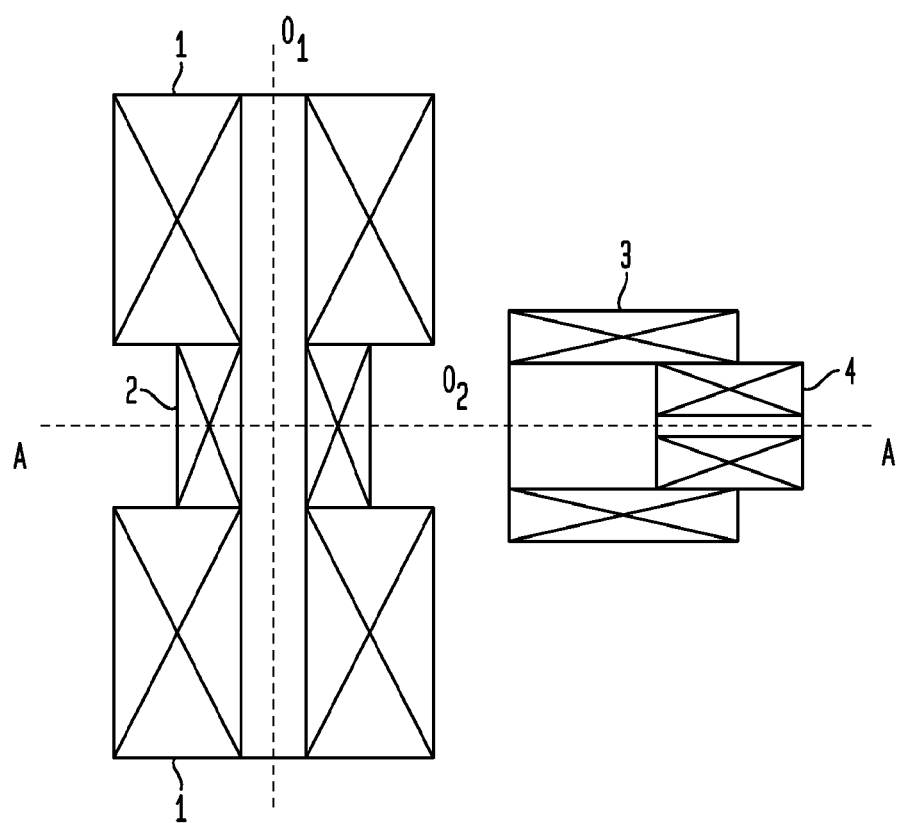
FIG. 2 presents a schematic of an example of a system of measuring the concentration of magnetic ballast.

In another embodiment, where a broad range of magnetic ballast concentration can be measured, the detection and reference coil assembly may be a symmetrical block, with a common plane of symmetry perpendicular to the detection set axis of symmetry, and which includes a reference set axis of symmetry. As shown in FIG. 2, such a configuration provides an absence of mutual inductance between the first and second detection coils 1, 2 and first and second reference coils 3, 4, and therefore provides the direct proportionality of measured voltage, or voltage differential, versus magnetite concentration, simplifying the procedure of calibration and measurement. The first and second detection coils and the first and second reference coils are positioned on a plane of symmetry perpendicular to each other.

Figure 3:
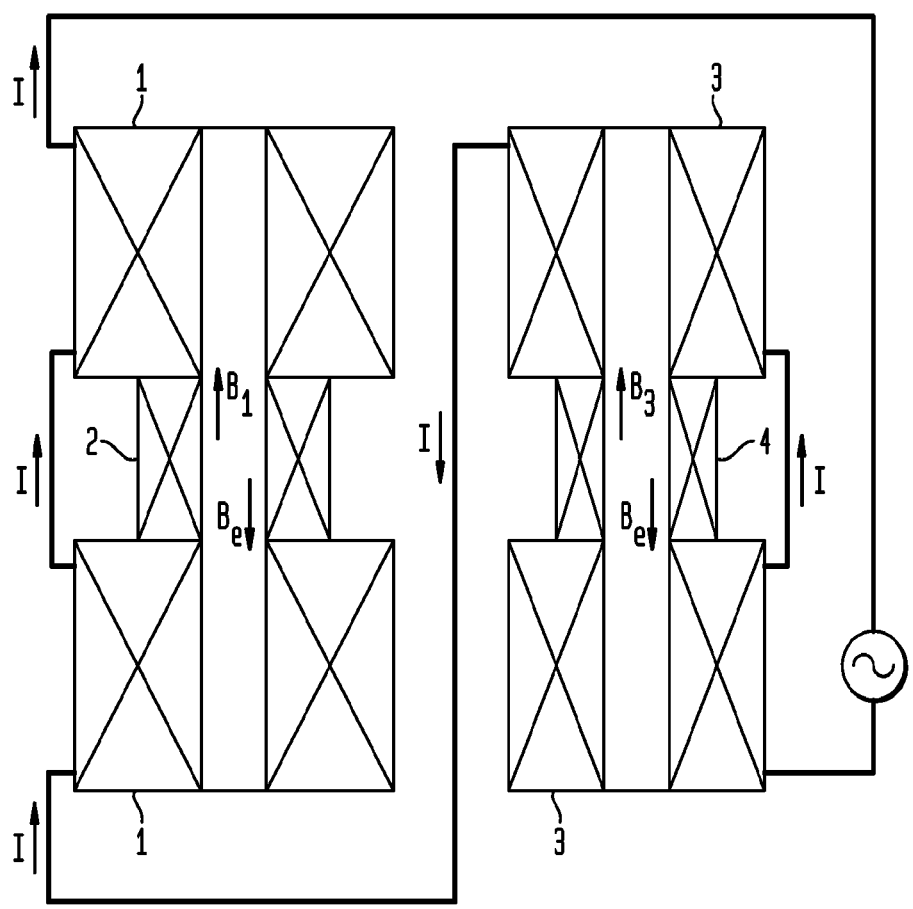
FIG. 3 presents a schematic of an example of a system of measuring the concentration of magnetic ballast.

In another embodiment, when in the vicinity of powerful electrical and/or electronic sources of parasitic electromagnetic field, the first and second detection coils 1,2 and first and second reference coils 3,4 assembly is a bloc of two identical sets, with a parallel axis of symmetry and with the same direction of the current (I) and excited magnetic field (Be) in the first detection coil and first reference coils. As shown in FIG. 3, such a configuration provides the mutual compensation for induced external magnetic field parasitic noise signals in the second detection coil 2 and second reference coil 4, and therefore provides higher measurement accuracy. Referring to FIG. 3, the values and direction for magnetic field (Be) in both detection coils 1,2 and reference coils 3,4 are the same. The values for magnetic fields (B1) and (B3) will be the same in the absence of a magnetic ballast slurry and different in the presence of a magnetic ballast slurry. The direction is the same. The first and second detection coils and the first and second reference coils may be positioned on a plane of symmetry parallel to each other.

Figure 4:
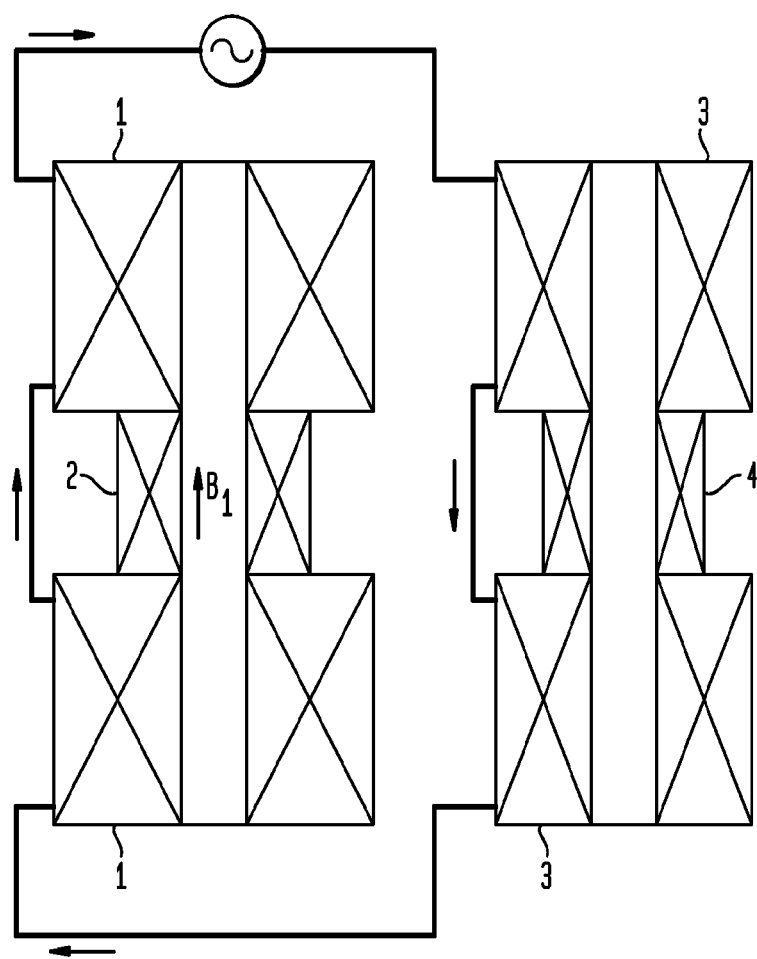
FIG. 4 presents a schematic of an example of a system of measuring the concentration of magnetic ballast.

In another embodiment, the detection coil and reference coil assembly is a block of two identical sets 1,2 and 3,4 with a parallel axis of symmetry and with an opposite direction of the current and the excited magnetic field in the first detection coil 1 and first reference coil 3. As shown in FIG. 4, such a configuration may provide compensation for the eddy currents in the ambient electro-conducting objects induced by detection and reference magnetic fields, and therefore may provide the compensation of the parasitic voltage induced by the magnetic field of these eddy currents in the secondary detection coil 2 and second reference coil 4, and therefore provides higher measurement accuracy. The directions of magnetic fields (B1 and B3) are different.

Figure 5:
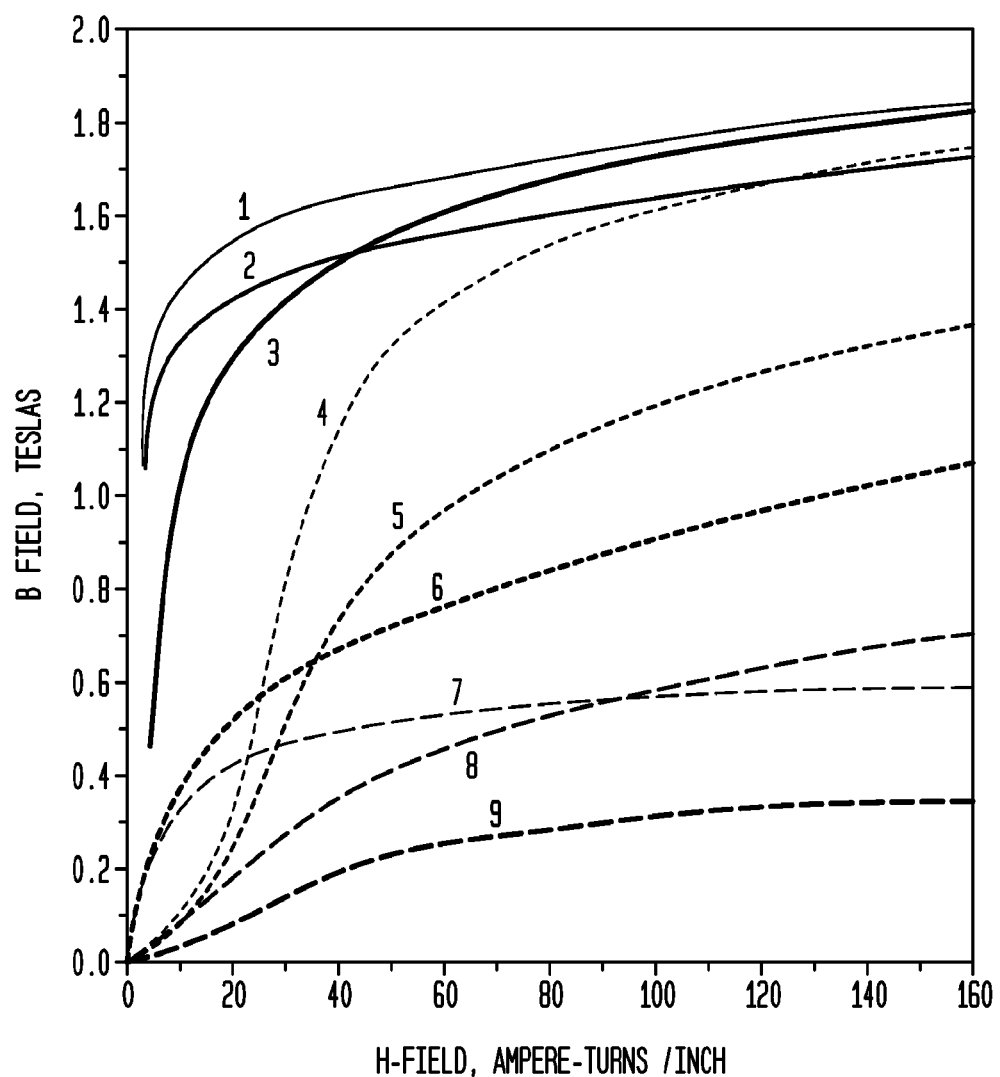
FIG. 5 presents a graph displaying a typical curve for magnetite magnetization.

In another embodiment, the magnetic field strength in the sample slurry is less than 500 A/m. A typical curve for magnetite magnetization is represented by line 9 FIG. 5.

This restriction provides the linear dependence of measured voltage versus magnetite concentration and its independence from the slurry flocculation quality, and therefore simplifies the calibration and measurement procedure and raises measurement accuracy.

In another embodiment, the position of the secondary reference coil 4 or its section(s) can be moved relative to the first reference coil 3 location and can be fixed at a position that provides equal or higher voltage induced in the second detection coil 2 than the voltage induced in second reference coil 4. This provides the monotonous change of measured voltage versus monotonous change of magnetic ballast concentration into the whole range, and therefore simplifies the calibration and measurement procedure and raises measurement accuracy.

The use of this apparatus enhances the operation and maintenance of water and waste water treatment systems that use magnetic ballast.

The new system and method for measuring the concentration of magnetic ballast in a slurry may be based upon inductive method. Specifically, the structure of the detection coil set is established, where the first detection coil is a pair of two identical sections that are placed symmetrically, one on each side of the second detection coil along a common axis, connected in series and carrying an equal electrical current in the same direction, producing a region of uniform magnetic field in the analyzed slurry.

In one embodiment, the systems and methods for measuring a concentration of magnetic ballast in a slurry, such as those described in FIGS. 1-4 may include measuring a concentration of a slurry in any one of the various components or subsystems of wastewater treatment systems, for example in U.S. Pat. No. 7,695,623, and U.S. Pat. No. 6,099,738 patent, or any other wastewater treatment system known to those skilled in the art that may utilize a magnetic ballast. For example, the magnetic ballast slurry may be provided from any of the various components of wastewater treatment system 100 of FIG. 5, such as aeration tank 102, clarifier 104 (including a sludge blanket in a clarifier), any of lines 106, 108, 110, 112, 114, 116, 118, or 120, tank 122 of weighting agent impregnation subsystem 124, return activated sludge subsystem 132, weighting agent recovery subsystem 134, and/or wasting subsystem 136. Further details regarding the operation of system 100 and the various components discussed above are disclosed in detail in the U.S. Pat. No. 7,695,623, incorporated herein by reference.

Figure 6:
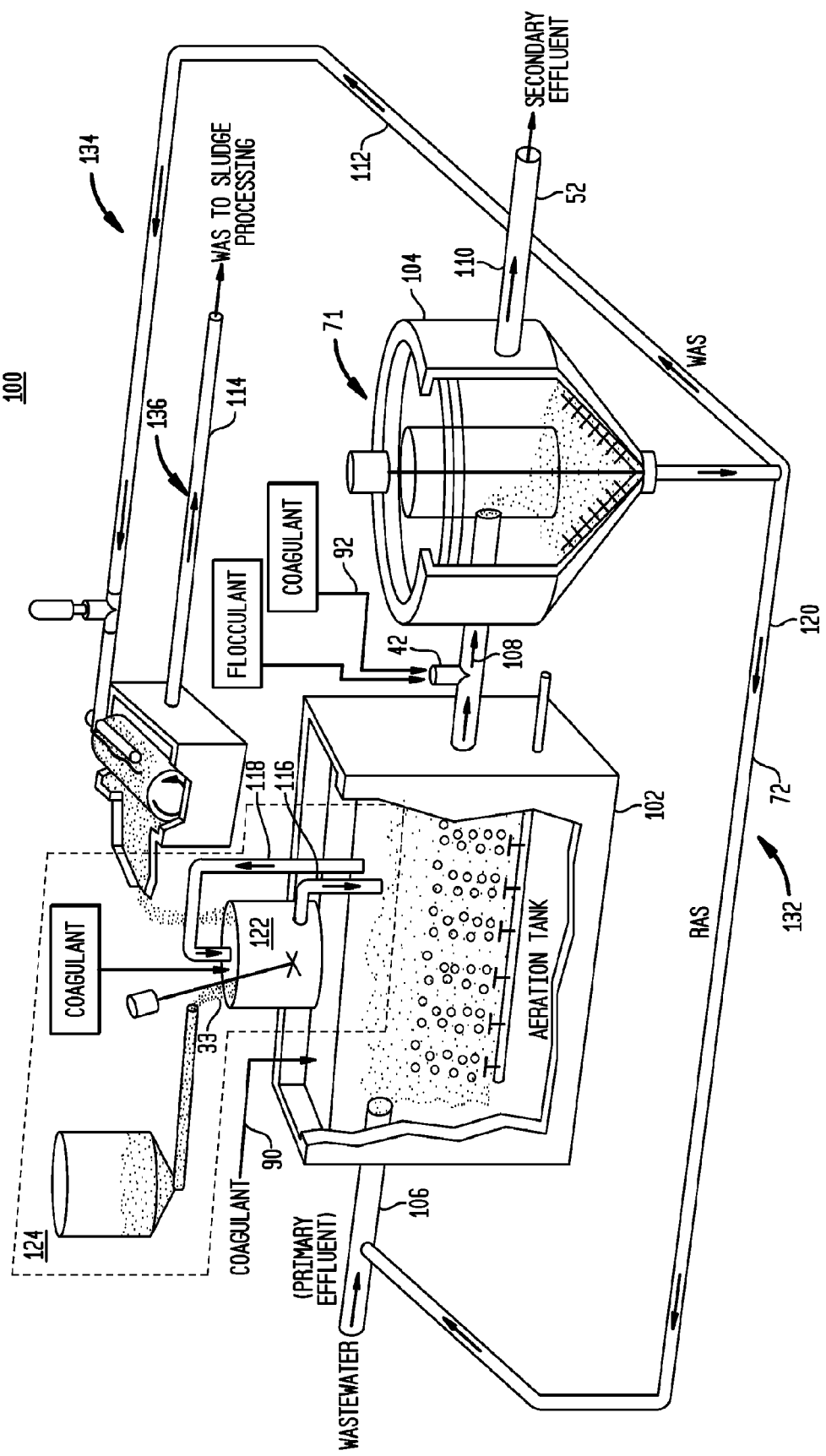
FIG. 6 presents a three-dimensional view showing components of a wastewater treatment system which may utilize the system for measuring the concentration of magnetic ballast.
Figure 7:
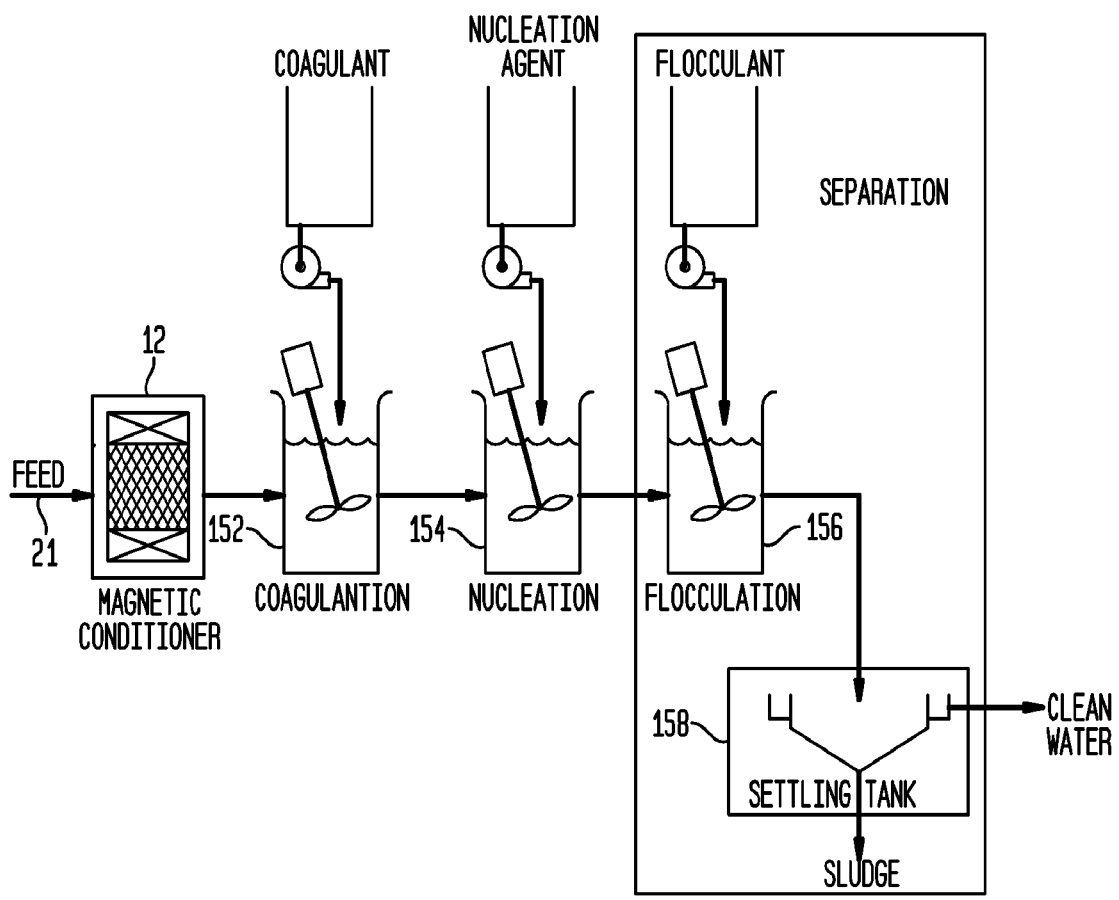
FIG. 7 presents a schematic block diagram showing components of another wastewater treatment system which can utilize the system for measuring the concentration of magnetic ballast.

The magnetic ballast slurry may be provided from any of the various components of wastewater treatment system including any of the various components from wastewater treatment system 150, of FIG. 6, as disclosed in U.S. Pat. No. 6,099,738, for example, a reaction tank, such as coagulation tank 152, nucleation tank 154 and/or flocculation tank 156. The slurry may also be provided from settling tank 158. Further details concerning the components and operation of wastewater treatment system 150 are disclosed in detail in U.S. Pat. No. 6,099,738, incorporated herein by reference.

The method for measuring the concentration of a magnetic ballast in slurry of this disclosure includes providing a detection conduit surrounded by a set of coaxial detection coils configured to receive the slurry, providing a reference conduit surrounded by a set of coaxial reference coils, and measuring the differential induced voltage between one of the set of coaxial detection coils and one of the set of coaxial reference coils to determine the concentration of the magnetic ballast in the slurry.

A method for measuring a concentration of magnetic ballast in a slurry may comprise providing a system comprising a detection conduit surrounded by a first detection coil, comprising a first section and a second section both positioned coaxially along the detection conduit; a reference conduit surrounded by a first reference coil; a second detection coil surrounding the detection conduit and positioned between the first and second sections of the first detection coil along a common axis of the detection conduit; and a second reference coil surrounding the reference conduit and positioned in proximity to the first reference coil. The method may comprise introducing the slurry into the detection conduit and generating a magnetic field in the first detection coil and the first reference coil. The method may further comprise measuring an induced differential voltage between the second detection coils and the second reference coil to determine the concentration of the magnetic ballast in the slurry based on the measured differential induced voltage.

Introducing the slurry into the detection conduit may comprise at least partially immersing the system in a component of a wastewater treatment system. The component may include a component selected from the group consisting of a reaction tank, a mixing tank, and aeration tank, a settling tank, a clarifier, a conduit, line or pipe, an impregnation subsystem, a return activated sludge subsystem, a weighting agent recovery subsystem, a wasting system, and combinations thereof. The concentration of the magnetic ballast in the slurry may be in a range of about 0.1 mg/l to about 500,000 mg/l.

In some embodiments, the method may include immersing the detection conduit in a slurry and disposing the reference conduit outside the component of the wastewater treatment system. The slurry may be a static slurry or a moving slurry.

It is to be appreciated that embodiments of the systems, apparatuses and methods discussed herein are not limited in application to the details of construction and the arrangement of the apparatus components and system operations as set forth in the above description or illustrated in the accompanying drawings. The apparatuses, systems and methods are capable of implementation in other embodiments and of being practiced or of being carried out in various ways. Examples of specific implementations are provided herein for illustrative purposes only and are not intended to be limiting. In particular, systems, apparatuses and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the apparatus and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. Any references to positional or spatial orientation are intended for convenience of description, not to limit the present apparatus and methods or their components.

Having described above several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

The invention claimed is:

1. A system for measuring a concentration of magnetic ballast in a slurry comprising:
    a detection conduit surrounded by a first detection coil, the detection conduit configured to receive the slurry, and the first detection coil comprising a first section and a second section both positioned coaxially along the detection conduit;
    a reference conduit surrounded by a first reference coil;
    a second detection coil surrounding the detection conduit and positioned between the first and second sections of the first detection coil along a common axis of the detection conduit;
    a second reference coil surrounding the reference conduit and positioned in proximity to the first reference coil, wherein the first and second detection coils and the first and second reference coils are positioned on a common plane of symmetry perpendicular to each other;
    an AC power source configured to generate a magnetic field in the first detection coil and the first reference coil; and
    a measurement device configured to measure a differential induced voltage between the second detection coil and the second reference coil to determine the concentration of the magnetic ballast in the slurry based on the measured differential induced voltage.

2. The system of claim 1, wherein the slurry is a static slurry.

3. The system of claim 1, wherein the slurry is a moving slurry.

4. The system of claim 1, wherein the first detection coil and the first reference coil are symmetrical.

5. The system of claim 1, wherein the first and second detection coils are identical to the first and second reference coils.

6. The system of claim 1, configured to measure a concentration of magnetic ballast in a range of about 0.1 mg/l to about 500,000 mg/l.

7. The system of claim 1, wherein the differential induced voltage between the second detection coil and the second reference coil voltage is proportional to the concentration of the magnetic ballast in the slurry.

8. A method for measuring a concentration of magnetic ballast in a slurry comprising:
    providing a system comprising:
        a detection conduit surrounded by a first detection coil, comprising a first section and a second section both positioned coaxially along the detection conduit;
        a reference conduit surrounded by a first reference coil;
        a second detection coil surrounding the detection conduit and positioned between the first and second sections of the first detection coil along a common axis of the detection conduit; and
        a second reference coil surrounding the reference conduit and positioned in proximity to the first reference coil, wherein the first and second detection coils and the first and second reference coils are positioned on a common plane of symmetry perpendicular to each other;
    introducing the slurry into the detection conduit;
    generating a magnetic field in the first detection coil and the first reference coil; and
    measuring an induced voltage between the second detection coils and the second reference coil to determine the concentration of the magnetic ballast in the slurry based on the measured differential induced voltage.

9. The method of claim 8, wherein introducing the slurry into the detection conduit comprises at least partially immersing the system in a component of a wastewater treatment system.

10. The method of claim 9, wherein the component includes a component selected from the group consisting of a reaction tank, a mixing tank, and aeration tank, a settling tank, a clarifier, a conduit, line or pipe, an impregnation subsystem, a return activated sludge subsystem, a weighting agent recovery subsystem, a wasting system, and combinations thereof.

11. The method of claim 8, wherein the concentration of the magnetic ballast in the slurry is in a range of about 0.1 mg/l to about 500,000 mg/l.

* * * * *